United States Patent
Lee et al.

(10) Patent No.: US 10,506,990 B2
(45) Date of Patent: Dec. 17, 2019

(54) DEVICES AND METHODS FOR FALL DETECTION BASED ON PHASE SEGMENTATION

(71) Applicant: QUALCOMM Incorporated, San Diego, CA (US)

(72) Inventors: Jin Won Lee, San Diego, CA (US); Xinzhou Wu, San Diego, CA (US); Rashid Ahmed Akbar Attar, San Diego, CA (US); Feng Han, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 308 days.

(21) Appl. No.: 15/261,561

(22) Filed: Sep. 9, 2016

(65) Prior Publication Data
US 2018/0070889 A1    Mar. 15, 2018

(51) Int. Cl.
*A61B 5/00* (2006.01)
*A61B 5/11* (2006.01)
(Continued)

(52) U.S. Cl.
CPC .......... *A61B 5/7282* (2013.01); *A61B 5/1117* (2013.01); *A61B 5/1122* (2013.01);
(Continued)

(58) Field of Classification Search
CPC .. A61B 5/1117; A61B 5/7282; G08B 21/0446
See application file for complete search history.

(56) References Cited

U.S. PATENT DOCUMENTS 4,357,491 A * 11/1982 Daaboul ............... H04J 3/175
                                                    704/233
5,361,104 A * 11/1994 Ohki ................... H04N 19/523
                                                    348/416.1
(Continued)

FOREIGN PATENT DOCUMENTS

CN         105342626 A        2/2016

OTHER PUBLICATIONS

Lewis, et al., "Do Wrist Guards Protect Against Fractures?", Jun. 1997, Annals of Emergency Medicine, American College of Emergency Physicians.*

(Continued)

*Primary Examiner* — Daniel L Cerioni
*Assistant Examiner* — Raymond P Dulman
(74) *Attorney, Agent, or Firm* — Weaver Austin Villeneuve & Sampson LLP (57) ABSTRACT

Aspects of the subject matter described in this disclosure can be implemented in a fall detection device and method. One or more motion sensors can access a user's acceleration data. The acceleration data can be segmented using a segmentation algorithm to identify a potential fall event. The segmentation algorithm can determine a cumulative sum of the acceleration data, where the cumulative sum is based on acceleration values being greater than or less than an acceleration threshold value, and a potential fall event can be identified where the cumulative sum is greater than a cumulative sum threshold value. Statistical features can be extracted from the segmented acceleration data and aggregated, and a determination can be made as to whether the potential fall event is a fall event based at least in part on the statistical features.

14 Claims, 7 Drawing Sheets

(51) Int. Cl.
  *G08B 21/04* (2006.01)
  *G16H 50/20* (2018.01)
  *G16H 40/63* (2018.01)
  *G16H 40/67* (2018.01)
  *G16H 50/30* (2018.01)
  *G16H 20/30* (2018.01)

(52) U.S. Cl.
  CPC .......... *A61B 5/6801* (2013.01); *A61B 5/7225* (2013.01); *A61B 5/7267* (2013.01); *G08B 21/0446* (2013.01); *G16H 40/63* (2018.01); *G16H 40/67* (2018.01); *G16H 50/20* (2018.01); *G16H 50/30* (2018.01); *A61B 2562/0219* (2013.01); *G16H 20/30* (2018.01)

(56) References Cited

U.S. PATENT DOCUMENTS

| | | | | |
|---|---|---|---|---|
| 7,961,109 | B2* | 6/2011 | Jang | A61B 5/0002 340/573.1 |
| 8,206,325 | B1* | 6/2012 | Najafi | A61B 5/1116 600/595 |
| 8,909,497 | B1* | 12/2014 | Shkolnikov | G01P 15/00 340/573.1 |
| 9,159,213 | B1* | 10/2015 | Chun | G08B 21/043 |
| 9,257,029 | B1* | 2/2016 | Hendrick, III | G08B 21/0415 |
| 2006/0214806 | A1 | 9/2006 | Clifford et al. | |
| 2006/0279426 | A1* | 12/2006 | Bonnet | A61B 5/1117 340/573.1 |
| 2006/0282021 | A1* | 12/2006 | DeVaul | A61B 5/0024 600/595 |
| 2008/0001735 | A1* | 1/2008 | Tran | G06F 19/3418 340/539.22 |
| 2008/0129518 | A1 | 6/2008 | Carlton-Foss | |
| 2008/0255795 | A1* | 10/2008 | Shkolnikov | G01C 21/165 702/141 |
| 2009/0048540 | A1* | 2/2009 | Otto | A61B 5/1117 600/595 |
| 2009/0121881 | A1 | 5/2009 | Fredricksson et al. | |
| 2009/0224925 | A1* | 9/2009 | Gannot | A61B 5/1117 340/573.1 |
| 2009/0292227 | A1* | 11/2009 | Scholten | A61B 5/0031 600/595 |
| 2009/0322540 | A1* | 12/2009 | Richardson | A61B 5/0002 340/573.7 |
| 2010/0121226 | A1* | 5/2010 | Ten Kate | A61B 5/1117 600/595 |
| 2010/0121603 | A1* | 5/2010 | Nyan | A61B 5/1117 702/141 |
| 2011/0246123 | A1* | 10/2011 | DelloStritto | A61B 5/11 702/141 |
| 2012/0143526 | A1* | 6/2012 | Benzel | A42B 3/046 702/42 |
| 2012/0223833 | A1* | 9/2012 | Thomas | G06F 19/3418 340/539.12 |
| 2013/0338453 | A1* | 12/2013 | Duke | A61B 5/7282 600/309 |
| 2014/0155705 | A1* | 6/2014 | Papadopoulos | A61B 5/0022 600/301 |
| 2014/0313036 | A1 | 10/2014 | Sweeney et al. | |
| 2016/0235356 | A1* | 8/2016 | Villard | A61B 5/00 |

OTHER PUBLICATIONS

Tasoulis, et al., Statistical Data Mining of Streaming Motion Data for Fall Detection in Assistive Environments, 2011, IEEE, 978-1-4244-4122-8/11, p. 3720-3723 (Year: 2011).*

International Search Report and Written Opinion, International Application No. PCT/US2017/046068, dated Nov. 16, 2017.

Noury et al., "A Proposal for the Classification and Evaluation of Fall Detectors", *Irbm, Elsevier*, vol. 29, No. 6, Nov. 28, 2008, pp. 340-349.

Pannurat et al., "Automatic Fall Monitoring: A Review", *Sensors*, vol. 14, No. 7, Jul. 18, 2014, pp. 12900-12936.

Tasoulis et al., "Statistical Data Mining of Streaming Motion Data for Fall Detection in Assistive Environments", 2011 Annual International Conference of the IEEE Engineering in Medicine and Biology Society, EMBC, Aug. 30, 2011, pp. 3720-3723.

* cited by examiner

FIGURE 6

DEVICES AND METHODS FOR FALL DETECTION BASED ON PHASE SEGMENTATION

TECHNICAL FIELD

This disclosure relates generally to fall detection devices and methods, and more particularly, to accurately detecting falls based on a segmentation algorithm using data gathered from one or more motion sensors.

DESCRIPTION OF RELATED TECHNOLOGY

Falls represent one of the biggest health risks for many people, especially the elderly. Approximately one in every three adults above 65 years of age fall each year, and approximate one in every two adults above 80 years old fall each year. Falls are the fifth leading cause of death over age 65, and about 10% of falls lead to major injury such as fractures and brain trauma hospitalization. Fast discovery of fall events can be critical in reducing injury and possibly preventing death. Fall detection devices are available, but many of them are not reliable and/or lack the ability to accurately detect a fall event.

Some conventional fall detection devices have the user press a call button to indicate a fall. However, in many instances of a fall, the user may become unconscious or may suffer from a severe injury. Some conventional fall detection devices send a signal when the person's orientation has changed to a horizontal position. However, such solutions produce too many false alarms or miss actual falls where the ending position is not horizontal, such as falls happening on stairs. Some fall detection devices use sophisticated cameras and special image analysis algorithms to determine whether a person has fallen in a room or area. However, image-based solutions suffer from problems such as privacy concerns and difficulty in effectively monitoring all areas where a fall may take place. Some conventional fall detection devices use data from motion sensors, including accelerometers and/or tilt sensors, to determine if acceleration values are above or below simple threshold values. However, while such fall detection devices may be worn by a user, they may implement motion sensors and algorithms that are not able to accurately and consistently distinguish between activities of daily living against actual falls. Such existing fall detection devices may produce false positives (i.e., identifying non-falls as falls), which can be costly, and may also produce false negatives (i.e., missing actual falls), which can be detrimental.

SUMMARY

The systems, methods and devices of this disclosure each have several aspects, no single one of which is solely responsible for the desirable attributes disclosed herein.

One aspect of the subject matter described in this disclosure can be implemented in a method of identifying a fall event. The method includes accessing acceleration data of an electronic device from one or more motion sensors and segmenting the acceleration data to identify a potential fall event, which includes determining a cumulative sum for the acceleration data and identifying the potential fall event if the cumulative sum is greater than a cumulative sum threshold value. The method further includes extracting one or more statistical features from the segmented acceleration data and determining whether the potential fall event is a fall event based at least in part on the one or more statistical features.

In some implementations, segmenting the acceleration data includes segmenting the acceleration data into at least three phases, where the at least three phases include (i) a before-fall phase, (ii) a during-fall phase, and (iii) an after-fall phase, where the during-fall phase includes the potential fall event. In some implementations, the method further includes analyzing the duration of time of the during-fall phase, where determining whether the potential fall event is a fall event is based at least in part on the duration of time of the during-fall phase. In some implementations, the one or more statistical features include one or more of the following: variance, maximum, minimum, $75^{th}$ percentile, $25^{th}$ percentile, mean, median, mean crossing rate, absolute area, or any combination thereof. In some implementations, the one or more statistical features include a mean crossing rate of acceleration extracted from the during-fall phase and variance of acceleration extracted from the after-fall phase. In some implementations, the electronic device is a wearable device. In some implementations, the one or more motion sensors consist of one or more accelerometers. In some implementations, the cumulative sum is based on acceleration values greater than or less than the first acceleration threshold value. The first acceleration threshold value and the cumulative sum threshold value are identified by a machine-learning algorithm. In some implementations, determining whether a potential fall event is a fall event includes aggregating the one or more statistical features from the segmented acceleration data, calculating a metric based on the one or more statistical features, and classifying the potential fall event as a fall event based at least in part on the calculated metric.

Another aspect of the subject matter described in this disclosure can be implemented in an electronic device for identifying a fall event. The electronic device includes one or more motion sensors configured to access acceleration data of the electronic device, a processor coupled to the one or more motion sensors, where the processor is configured to segment the acceleration data to identify a potential fall event, extract one or more statistical features from the segmented acceleration data, and determine whether the potential fall event is a fall event based at least in part on the one or more statistical features, where the processor configured to segment the acceleration data is configured to determine a cumulative sum for the acceleration data and identify a potential fall event if the cumulative sum is greater than a cumulative sum threshold value.

In some implementations, the processor configured to segment the acceleration data is configured to segment the acceleration data into at least three phases, where the at least three phases include (i) a before-fall phase, (ii) a during-fall phase, and (iii) an after-fall phase, where the during-fall phase includes the potential fall event. In some implementations, the one or more statistical features include a mean crossing rate of acceleration extracted from the during-fall phase and variance of acceleration extracted from the after-fall phase. In some implementations, the electronic device is a wearable device and the one or more motion sensors consist of one or more accelerometers. In some implementations, the electronic device further includes a low-pass filter configured to smooth out the acceleration data accessed from the one or more motion sensors.

Another aspect of the subject matter described in this disclosure can be implemented in an electronic device for identifying a fall event. The electronic device includes means for accessing acceleration data and means for analyzing the acceleration data coupled to the means for accessing acceleration data, the means for analyzing the acceleration data configured to segment the acceleration data to identify a potential fall event, extract one or more statistical features from the segmented acceleration data, and determine whether the potential fall event is fall event based at least in part on the one or more statistical features, where the means for analyzing the acceleration data configured to segment the acceleration data is configured to determine a cumulative sum for the acceleration data and identify a potential fall event if the cumulative sum is greater than a cumulative sum threshold value.

In some implementations, the means for analyzing the acceleration data configured to segment the acceleration data is configured to segment the acceleration data into at least three phases, where the at least three phases include (i) a before-fall phase, (ii) a during-fall phase, and (iii) an after-fall phase, where the during-fall phase includes the potential fall event, and where the one or more statistical features include: a mean crossing rate of acceleration extracted from the during-fall phase and variance of acceleration extracted from the after-fall phase. In some implementations, the electronic device is a wearable device and the one or more motion sensors consist of one or more accelerometers.

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale.

BRIEF DESCRIPTION OF THE DRAWINGS

Like reference numbers and designations in the various drawings indicate like elements.

DETAILED DESCRIPTION

The following description is directed to certain implementations for the purposes of describing various aspects of this disclosure. However, a person having ordinary skill in the art will readily recognize that the teachings herein can be applied in a multitude of different ways. Various embodiments will be described in detail with reference to the accompanying drawings. References made to particular examples and implementations are for illustrative purposes, and are not intended to limit the scope of the claims.

The described implementations may be implemented in any device, apparatus, or system that includes a sensor system. In addition, it is contemplated that the described implementations may be included in or associated with a variety of electronic devices such as, but not limited to: mobile telephones, multimedia Internet enabled cellular telephones, mobile television receivers, wireless devices, smartphones, smart cards, wearable devices such as bracelets, armbands, wristbands, rings, headbands, patches, belts, etc., Bluetooth® devices, personal data assistants (PDAs), wireless electronic mail receivers, hand-held or portable computers, netbooks, notebooks, smartbooks, tablets, global navigation satellite system (GNSS) receivers/navigators, cameras, digital media players (such as MP3 players), camcorders, game consoles, wrist watches, electronic reading devices (e.g., e-readers), mobile health devices, etc. By way of example, the described implementations may be implemented in a wearable device. Some implementations of the wearable device may be a health-monitoring device worn by a user. However, the wearable device may have other capable of other applications, such as making/receiving phone calls, transmitting/receiving text messages, transmitting/receiving emails, keeping time, performing navigation, playing music, etc. Thus, the teachings are not intended to be limited to the implementations depicted solely in the Figures, but instead have wide applicability as will be readily apparent to one having ordinary skill in the art.

This disclosure relates generally to devices and methods for identifying a fall event. A fall detection device can include one or more motion sensors for collecting a user's acceleration data over time. The acceleration data can be processed and analyzed by applying a segmentation algorithm. The segmentation algorithm identifies a potential fall in the acceleration data, and segments the acceleration data into one or more phases, such as: (1) a before-fall phase, (2) a during-fall phase, and (3) an after-fall phase. Statistical features are extracted from each of the phases or from at least some of the phases, where examples of statistical features include: variance, maximum, minimum, $75^{th}$ percentile, $25^{th}$ percentile, mean, median, mean crossing rate, absolute area, and combinations thereof. The statistical features from at least some of the phases are aggregated and the potential fall event is classified as a fall event using a classifier trained by a machine-learning algorithm.

Particular implementations of the subject matter described in this disclosure can be implemented to realize one or more of the following potential advantages. The fall detection device and method of the present disclosure can more accurately and reliably distinguish genuine fall events from activities of daily living. This reduces the likelihood of producing false positives and minimizes the risk of producing false negatives. Specifically, the present disclosure can detect genuine fall events by analyzing statistical features across different phases, rather than analyzing one statistical feature or multiple statistical features in a smaller or unsegmented window. That way, instead of just looking at an unsegmented window encompassing a possible fall event, statistical features from a before-fall phase and statistical features from an after-fall phase can provide additional valuable information for determining whether a genuine fall event occurred. Moreover, the segmentation algorithm can further increase accuracy and reliability by segmenting acceleration data of a user into the different phases with a high level of precision. The segmentation algorithm can more accurately and reliably identify possible fall events by using a cumulative sum of acceleration data and comparing the cumulative sum to threshold values, rather than using acceleration data and comparing the acceleration data to threshold values. A machine-learning algorithm can be implemented in the present disclosure to train a classifier and more accurately classify a possible fall event as a genuine fall event. Whereas the accuracy of conventional fall detection devices can be less than 95%, the accuracy of the fall detection device of the present disclosure can be greater than 95%, or even greater than 98%. In some implementations, the present disclosure may reduce power consumption by collecting acceleration data without collecting or analyzing angular velocity, orientation, image data, or other monitoring data that can consume power in a fall detection device. In some implementations, the fall detection device can be a wearable device that can improve convenience and tracking with the user. The wearable device can be noninvasive, nonrestrictive to ambulatory use, and enable continuous monitoring of the user's activities.

Figure 1:
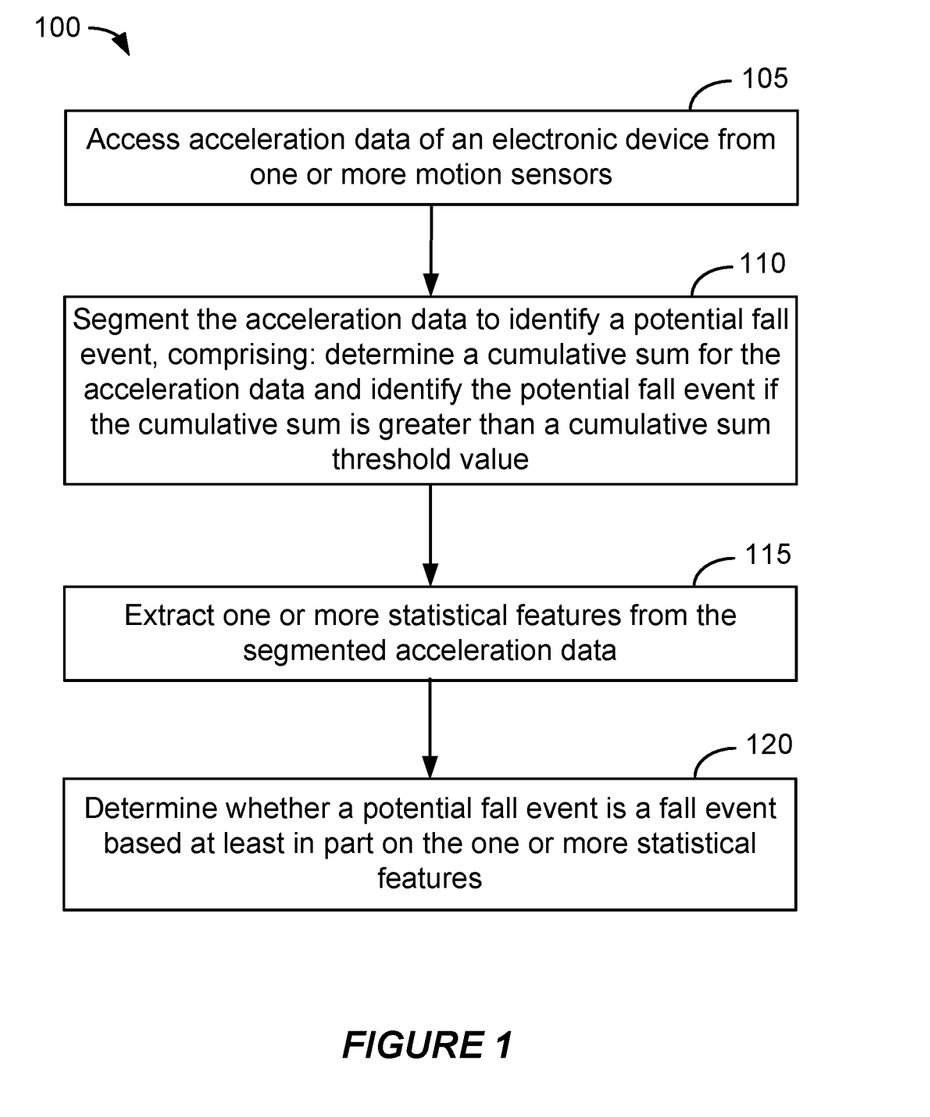
FIG. 1 shows a flow diagram illustrating an example process for identifying a fall event according to some implementations.

FIG. 1 shows a flow diagram illustrating an example process for identifying a fall event according to some implementations. The blocks of the process 100 are not necessarily performed in the order indicated. Moreover, the blocks of the process 100 may include more or fewer blocks than shown and/or described. Although some blocks of the process 100 are described as being performed by a single processor, in some implementations more than one processor may be involved in performing these operations. For example, more than one processor of a control system may be involved in performing these operations. In some implementations, the blocks of the process 100 can be performed by a device shown in FIG. 5, or by a device shown in FIG. 6, as described below. In some implementations, the blocks of the process 100 may be implemented, at least in part, according to software stored on one or more non-transitory computer readable media.

At block 105 of the process 100, acceleration data of an electronic device is accessed from one or more motion sensors. The electronic device may be associated with a user of the electronic device. The one or more motion sensors can include one or more accelerometers. The one or more accelerometers can be, for example, three linear accelerometers that measure linear acceleration data along a particular orthogonal axis of a Cartesian coordinate system or a single three-dimensional accelerometer. In some implementations, the one or more motion sensors consist only of one or more accelerometers, which can improve power savings. In some implementations, the one or more motion sensors can be part of a wearable device, such as a wrist-worn wearable device.

In some implementations, additional data may be accessed from the one or more motion sensors, such as data regarding the user's angular acceleration, angular velocity, rotation, magnetic field, force, orientation, and the like. In some implementations, the process 100 can further include accessing angular velocity data and orientation data from the one or more motion sensors. For example, the angular velocity data and the orientation data may be accessed from one or more gyroscopes and one or more magnetometers. Such data can also be subsequently segmented and analyzed along with the acceleration data of the user.

The acceleration data, also referred to as "linear acceleration data," "motion data," "acceleration curve," or "accelerometer reading," provides the linear acceleration of the user over time. In some implementations, the acceleration data can be invariant of direction. For example, the acceleration magnitude in the acceleration data is independent of the linear acceleration along a particular orthogonal axis of a Cartesian coordinate system (e.g., $a=\sqrt{(a_x^2+a_y^2+a_z^2)}$). As a result, falls can be detected regardless of whether someone is falling backwards, forwards, sideways, etc. When there is no motion, the acceleration magnitude in the acceleration data may only show the force of gravity. Variations in acceleration magnitudes can be attributable to routine motion, such as walking, running, sitting down, picking up an object, swinging arms, etc.

Falls can generally be characterized as uncontrolled downward movement of a user from a higher position to a lower position. Falls can happen in a number of ways. Examples include tripping or stumbling while walking forward, shifting of body weight while sitting down, shifting of body weight while getting up, shifting of body weight while walking forward, shifting of body weight while initiating walking, hitting or bumping while standing, loss of consciousness while walking forward, loss of support with an external object during sitting down, loss of support with an external object while getting up, etc. When people fall, they usually go into free fall until at least a portion of their body impacts the ground, and they reach a stable equilibrium.

Figure 4A:
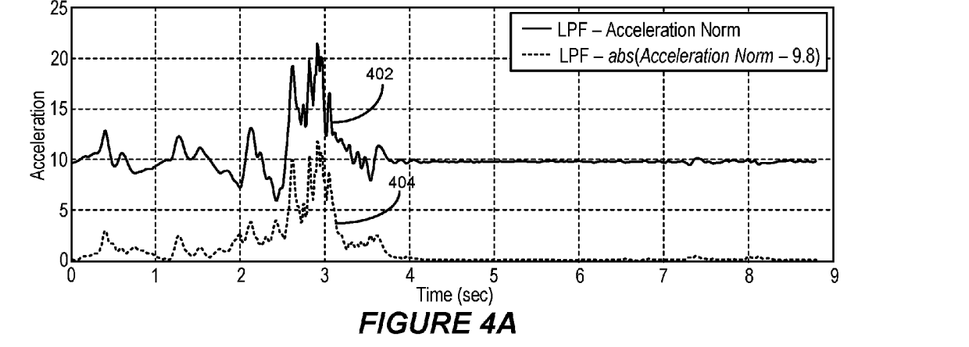
FIG. 4A shows an example plot of acceleration data as a function of time.

In some implementations, the acceleration data can be processed by a filter. Since cumulative motion of a user is mostly low in frequency, a low-pass filter can filter out acceleration values that fluctuate significantly. The filter can smooth out the acceleration data. In addition, the acceleration data can account for the acceleration of the user by subtracting out the force of gravity. That way, what is identified in the acceleration data is linear acceleration of the user. FIG. 4A shows an example plot of acceleration data as a function of time. The plot includes normalized acceleration data after being processed by a low-pass filter, and also includes normalized acceleration data after being processed by a low-pass filter and subtracting out the force of gravity. In FIG. 4A, the user exhibits movement including some variations of motion for the first few seconds, followed by several localized spikes in acceleration in the next few seconds, and followed by a stable equilibrium without variations in acceleration in the remaining seconds. The localized spikes in acceleration may reflect the uncontrolled movement of the user as well as the force of impact. The acceleration data in FIG. 4A may indicate a potential fall event.

Typical fall detection devices that implement motion sensors can focus almost exclusively on the abrupt localized spikes in acceleration to detect fall events. In addition or in the alternative, typical fall detection devices analyze the acceleration data across a data window without segmenting into different phases. In addition or in the alternative, typical fall detection devices may utilize other sensors for data collection, such as gyroscopes and orientation sensors, which can significantly add to the power consumption of the fall detection device.

At block 110 of the process 100, the acceleration data is segmented to identify a potential fall event, which includes a cumulative sum for the acceleration data being determined and the potential fall event being identified if the cumulative sum is greater than a cumulative sum threshold value. In some implementations, the acceleration data is segmented into at least three phases. Each phase can represent a window of time in the acceleration data. The at least three phases can include: (1) a before-fall phase, (2) a during-fall phase, and (3) an after-fall phase. The acceleration data accessed by the one or more motion sensors at block 105 can be segmented using a segmentation algorithm. As a result, the acceleration data can be precisely analyzed in different segments. Segmentation of the acceleration data using a segmentation algorithm is described further in a process 200 in FIG. 2.

Figure 2:
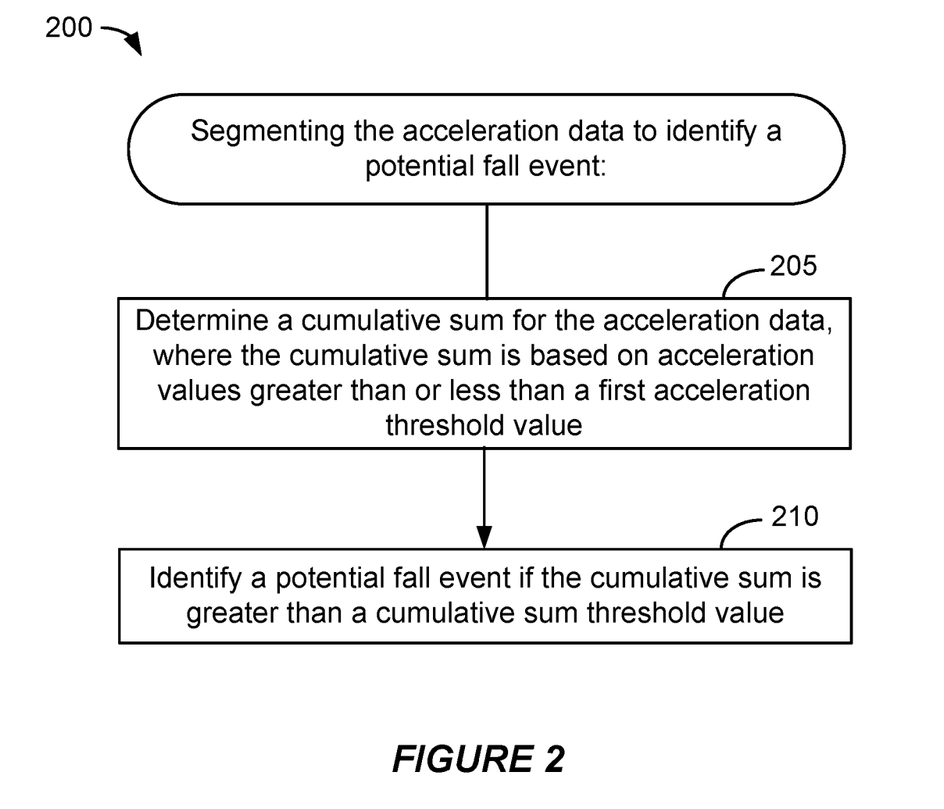
FIG. 2 shows a flow diagram illustrating an example process for segmenting acceleration data to identify a potential fall event according to some implementations.

FIG. 2 shows a flow diagram illustrating an example process for segmenting acceleration data to identify a potential fall event according to some implementations. The process 200 may be performed in a different order or with different, fewer, or additional operations. The blocks of the process 200 may be performed by one or more processors. In some implementations, the blocks of the process 200 may be performed by a device shown in FIG. 5, or by a device shown in FIG. 6, as described below. In some implementations, the blocks of the process 200 may be implemented, at least in part, according to software stored on one or more non-transitory computer readable media.

An example segmentation algorithm of the process 200 computes a cumulative sum (CUSUM) according to a CUSUM algorithm. At block 205 of the process 200, a cumulative sum for the acceleration data is determined. In some implementations, the cumulative sum can be based on acceleration values being greater than or less than a first acceleration threshold value. In some implementations, a first acceleration threshold value ($A_{th1}$) and a cumulative sum threshold value ($C_{th}$) are identified. One or both of $A_{th1}$ and $C_{th}$ are values that can be incorporated in the CUSUM algorithm. These threshold values are not arbitrarily determined, but may be determined from data-driven analysis. For example, these threshold values may be identified by conducting or gathering data from a series of fall events. In some implementations, $A_{th1}$ and $C_{th}$ may be identified from a machine-learning algorithm. In some implementations, the process 200 may further include identifying a second acceleration threshold value ($A_{th2}$). In some implementations, the cumulative sum can also be based on acceleration values being less than the second acceleration threshold value.

Acceleration values are cumulatively summed together, where acceleration values greater than $A_{th1}$ increase the CUSUM values and acceleration values less than $A_{th1}$ or less than $A_{th2}$ decrease the CUSUM values. Rather than doing an instantaneous decision whenever an acceleration value is higher than a threshold to determine if a fall event has occurred or not, the CUSUM algorithm takes into consideration the sum of acceleration values, where the sum is increased for acceleration values higher than $A_{th1}$.

Figure 4B:
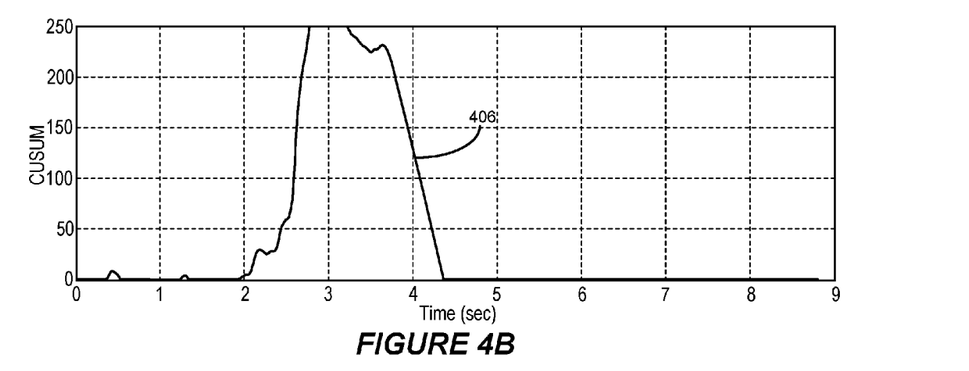
FIG. 4B shows an example plot of a cumulative sum as a function of time.

The CUSUM algorithm may be better understood by considering the examples in FIGS. 4A-4E. In FIG. 4A, a first curve 402 represents an acceleration norm after low-pass filtering (LPF). A second curve 404 in FIG. 4A represents absolute values of the difference between the acceleration norm and the gravitational acceleration after low-pass filtering. As used herein, values of the second curve 404 are referred to as linear acceleration values. In this example, the quantities represented in the second curve 404 are used for the determination of CUSUM according to the disclosed implementations. Here, a first acceleration threshold value can be set to 2.5. During the interval from 2 seconds to 3 seconds, some of the linear acceleration values greater than 2.5 in the second curve 404 are greater than 2.5, and thus, a positive value (i.e., a difference between the linear acceleration value and the first acceleration threshold value) is added to respective CUSUM values. A respective CUSUM curve 406 is shown in FIG. 4B. In contrast, after 3 seconds, some of the linear acceleration values fall below 2.5, and thus, negative values (i.e., a difference between the linear acceleration value and the first acceleration threshold value) are accumulated to respective CUSUM values. However, CUSUM does not go below zero, and thus, it is clipped at zero when the CUSUM value becomes negative as shown in FIG. 4B.

Figure 4C:
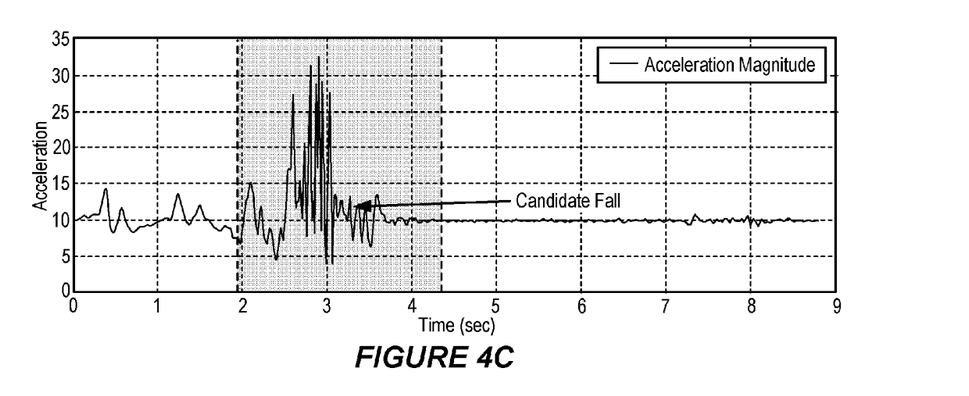
FIG. 4C shows an example plot of the acceleration data after segmentation.
Figure 4D:
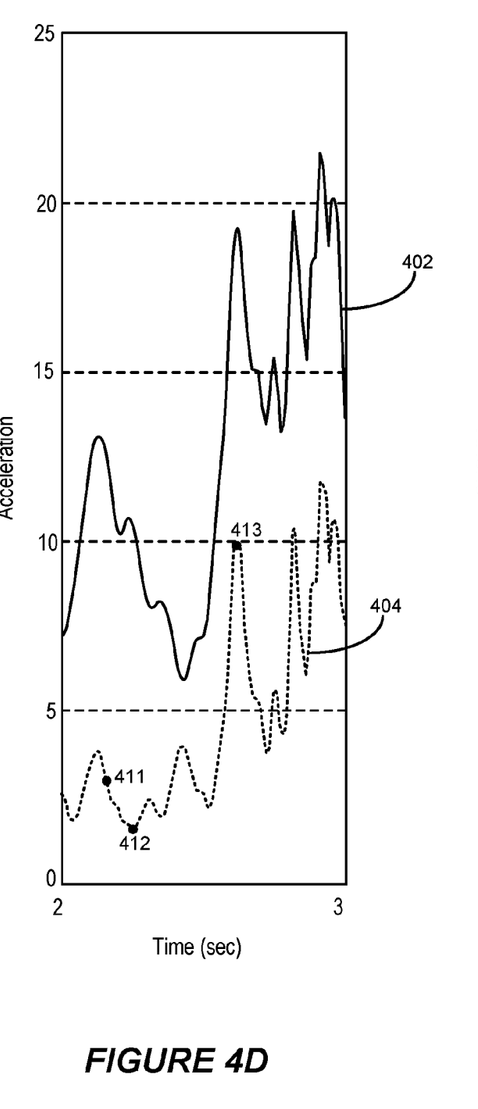
FIG. 4D shows a magnified view of the example plot of the acceleration data as a function of time in FIG. 4A.
Figure 4E:
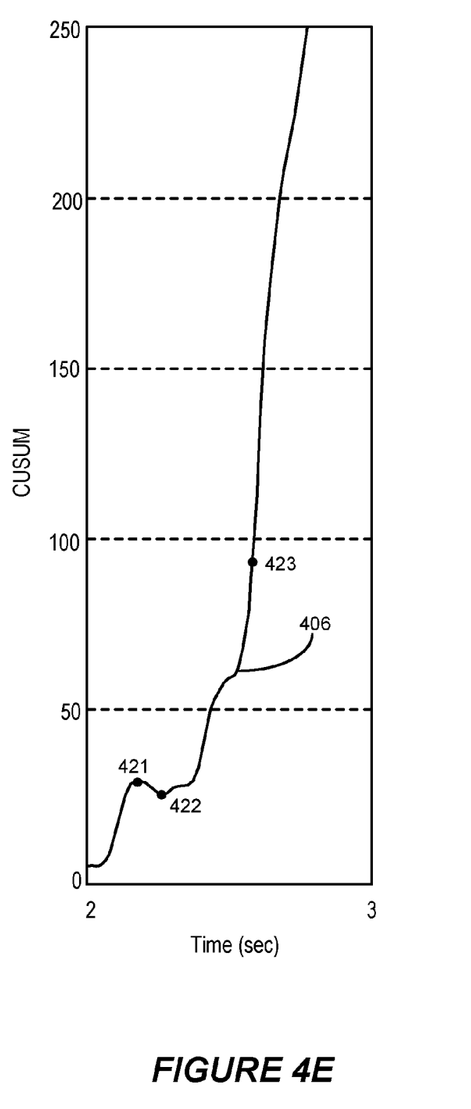
FIG. 4E shows a magnified view of the example plot of the cumulative sum as a function of time in FIG. 4B.

FIG. 4D shows a magnified view of the curves 402, 404 in FIG. 4A between 2 seconds and 3 seconds, and FIG. 4E shows a magnified view of the CUSUM curve 406 in FIG. 4B between 2 seconds and 3 seconds. To illustrate, if the CUSUM algorithm is represented by the formula: CUSUM[i]=max(0, CUSUM[i−1]+acceleration[i]−$A_{th1}$), where CUSUM[0]=0 and $A_{th1}$=2.5 for the second curve 404 of FIGS. 4A and 4D, then the CUSUM curve 406 can be represented in FIGS. 4B and 4E. At point 411 in FIG. 4D, the linear acceleration value is greater than 2.5 by about 0.5. If a previous respective CUSUM value for CUSUM[i−1] was 22.5, then 0.5 is added to 22.5 so that the CUSUM curve 406 reaches a value of 23.0 at point 421 in FIG. 4E. At point 412 in FIG. 4D, the linear acceleration value is less than 2.5 by about 1.0. Assuming the previous respective CUSUM value for CUSUM[i−1] was 23.0 at point 421, then 1.0 is subtracted from 23.0 so that the CUSUM curve 406 reaches a value of 22.0 at point 422 in FIG. 4E. The CUSUM curve 406 can increase or decrease depending on the difference between the linear acceleration value and $A_{th1}$, which adds to or subtracts from the previous CUSUM value. At point 413 of the second curve 404, the difference between the linear acceleration value and $A_{th1}$ is about 7.5, which is added to a previous respective CUSUM value to increase the CUSUM value at point 423.

At block 210 of the process 200, a potential fall event is identified if the cumulative sum is greater than a cumulative sum threshold value ($C_{th}$). When the CUSUM is greater than $C_{th}$, then this is indicative that a potential fall event has occurred.

FIG. 4B shows an example plot of a cumulative sum as a function of time. The CUSUM curve 406 represents the CUSUM of the acceleration data in FIG. 4A across time, where CUSUM is based on acceleration values greater than or less than the first acceleration threshold value. As shown in FIG. 4B, the CUSUM curve 406 increases after 2 seconds. Between 2 seconds and 3 seconds, the CUSUM curve 406 reaches a value greater than 250, where $C_{th}$=250. After 3 seconds, the CUSUM curve 406 begins to taper and decrease. After 4 seconds, the CUSUM curve 406 reaches zero.

Segmentation can occur at locations where CUSUM equals zero. Specifically, where a CUSUM is zero right before increasing in value towards $C_{th}$, that point in time can indicate the start of the during-fall phase. In addition, where CUSUM is zero after decreasing in value from $C_{th}$, that point in time can indicate the end of the during-fall phase. In other words, from where CUSUM reaches $C_{th}$, a beginning of the during-fall phase can be located by tracing backwards until CUSUM is zero, and an end of the during-fall phase can be located by tracing forwards until CUSUM is zero. In FIG. 4B, the beginning of the during-fall phase can occur around 1.95 seconds and the end of the during-fall phase can occur around 4.30 seconds. After such points are located, a before-fall phase, a during-fall phase, and an after-fall phase can be identified, where the potential fall event can be identified within the during-fall phase. Not only can the CUSUM algorithm identify a potential fall event and segment acceleration data, but the CUSUM algorithm can also precisely establish the beginning and end points of the different phases.

FIG. 4C shows an example plot of the acceleration data after segmentation. The acceleration data in FIG. 4C may reflect the acceleration values of the user without being processed by a filter, such as a low-pass filter. FIG. 4C shows a before-fall phase on the left-hand side, where the before-fall phase can occur before about 1.95 seconds. FIG. 4C shows a during-fall phase highlighted in the middle, where the during-fall phase can occur between about 1.95 seconds and about 4.30 seconds. FIG. 4C shows an after-fall phase on the right-hand side, where the after-fall phase can occur after about 4.30 seconds. The plot of the acceleration data has been segmented so that a potential fall event is indicated in the during-fall phase.

Returning to FIG. 2, in some implementations of the process 200, the cumulative sum for the acceleration data can be determined where a CUSUM value increases when an acceleration value is greater than the first acceleration threshold value ($A_{th1}$) and where the CUSUM value decreases when an acceleration value is less than a second acceleration threshold value ($A_{th2}$). While $A_{th1}$ can be the threshold value before CUSUM reaches $C_{th}$, $A_{th2}$ can be the threshold value after CUSUM reaches $C_{th}$. For example, $A_{th2}$ can be greater than $A_{th1}$ so that the CUSUM decreases more quickly after CUSUM reaches $C_{th}$. In some implementations, $A_{th1}$ and $A_{th2}$ can be the same. In some implementations, $A_{th1}$ and $A_{th2}$ can be different.

The CUSUM algorithm can take various formulations, where linear acceleration of the user is cumulatively summed over time and increases where the linear acceleration is greater than a threshold value. By way of example, a CUSUM algorithm can have the following algorithm: CUSUM[i]=max(0, CUSUM[i−1]+acceleration[i]−$A_{th1}$), where CUSUM[0]=0, and where $A_{th1}$ is the first acceleration threshold value and acceleration[i] is the linear acceleration magnitude at time [i], and where i>0. If CUSUM[i] is greater than $C_{th}$, the CUSUM algorithm determined that a fall event has occurred, where $C_{th}$ is the cumulative sum threshold value. In some implementations, after reaching $C_{th}$, the CUSUM algorithm can change to the following algorithm: CUSUM[i]=max(0, CUSUM[i−1]+acceleration[i]−$A_{th2}$), where $A_{th2}$ is the second acceleration threshold value.

After the acceleration data has been segmented according to a segmentation algorithm, the duration of each of the phases can be established using minimum and maximum time duration. In some implementations of the process 200, the before-fall phase can be identified as before the during-fall phase within certain minimum and maximum time duration. For example, the before-fall phase can be established within a time frame of greater than 0 seconds but less than or equal to 20 seconds, or greater than 1 second but less than or equal to 10 seconds. In some implementations of the process 200, the after-fall phase can be identified as after the during-fall phase within certain minimum and maximum time duration. For example, the after-fall phase can be established within a time frame of greater than 1 second but less than or equal to 30 seconds, or greater than 5 seconds but less than or equal to 20 seconds. In some implementations, the duration of the before-fall phase and the duration of the after-fall phase can be established using maximum time duration only. This can be used to trace back the beginning point of the before-fall phase from the beginning point of the during-fall phase, and trace forward to the end point of the after-fall phase from the end point of the during-fall phase.

In some implementations, the process 100 further includes accessing angular velocity data and orientation data from the one or more motion sensors, and segmenting the angular velocity data and the orientation data. The angular velocity data and the orientation data can be segmented into at least three phases. Such data can be used to supplement the acceleration data of the user.

Returning to FIG. 1, at block 115 of the process 100, one or more statistical features are extracted from the segmented acceleration data. Where the acceleration data is segmented into at least three phases, the one or more statistical features can be extracted from at least some of the phases. Analysis of the acceleration data can be performed separately for some of the phases, or for each of the phases, where the analysis extracts information from the phases and combines the information to subsequently determine if a fall event has occurred. The extracted information can be statistical features, where the one or more statistical features include one or more of the following: variance, maximum, minimum, $75^{th}$ percentile, $25^{th}$ percentile, mean, median, mean crossing rate, absolute area, and combinations thereof. While the extracted statistical features can be extracted statistical features of the acceleration data, the extracted statistical features can also constitute statistical features of the angular velocity and/or orientation data from at least some of the phases.

Variance can measure how far a set of acceleration values spread out from the mean, and can be the square of the standard deviation. Maximum can represent the largest acceleration value within a sample. Minimum can represent the smallest acceleration value within a sample. $75^{th}$ percentile can represent the acceleration value below which 75% of the acceleration data fall below. $25^{th}$ percentile can represent the acceleration value below which 25% of the acceleration data fall below. Mean can represent the average acceleration value divided against all acceleration values. Median can represent the middle acceleration value from the list of all acceleration values. Mean crossing rate can represent the number of times that the acceleration data crosses the mean divided over time. Absolute area can represent the total area under a curve for the acceleration data, which can provide a measure of the summation of the acceleration values in a particular phase. While the aforementioned statistical features are discussed with reference to acceleration data, it is understood that the statistical features can be applied to other data, such as angular velocity data and orientation data.

Some of the aforementioned statistical features can be extracted for particular phases of the acceleration data, which can provide more useful information than if the aforementioned statistical features were extracted from the entirety of the acceleration data. In some implementations, a mean crossing rate of the acceleration data is extracted from the during-fall phase. In the duration of a fall event, there can be a lot of fluctuation in linear acceleration. Parts of the body may be moving rapidly, such as the arms and hands, thereby leading to the fluctuations in linear acceleration. These parts of the body can be moving rapidly forwards and backwards. A high value of a mean crossing rate can be indicative of an actual fall event. In some implementations, a variance of the acceleration data is extracted from the after-fall phase. After a fall event, a person may be relatively immobile or even unconscious, thereby leading to a generally stable equilibrium of linear acceleration. A low variance can reinforce data supporting indication of an actual fall event. In some implementations, a maximum acceleration value can be extracted from the during-fall phase. A sufficiently high maximum acceleration value can be indicative of an actual fall event. In some implementations, an absolute area of the acceleration data can be extracted from the after-fall phase. A sufficiently low absolute area can be indicative of an actual fall event.

In addition to extracting one or more statistical features from the acceleration data, one or more statistical features may be extracted from angular velocity data and/or orientation data. After segmentation, useful information can be ascertained from the angular velocity data and orientation data. In some implementations, a variance of angular velocity can be extracted from the during-fall phase. With rapid changes in angular velocity during a fall, a high variance can be indicative of an actual fall event. In some implementations, a maximum angular velocity can be extracted from the during-fall phase. A sufficiently high maximum angular velocity can be indicative of an actual fall event. In some implementations, a minimum angular velocity can be extracted from the after-fall phase. A sufficiently low minimum angular velocity can be indicative of an actual fall event. In some implementations, a median of orientation can be extracted from the after-fall phase. If the orientation of the user was more horizontal than vertical in the after-fall phase, then that would be more indicative of an actual fall event.

In some implementations of the process 100, the duration of time of at least one of the phases can also be analyzed. The duration of time of at least one of the phases can be calculated after segmenting the acceleration data. For example, the duration of time of the during-fall phase in FIG. 4C is calculated to be about 2.35 seconds. In some implementations, the duration of time of the during-fall phase can be compared to a minimum threshold value and a maximum threshold value. The during-fall phase may not be too short compared to an actual fall, so as to distinguish from abbreviated activities such as an abrupt movement or movements. The during-fall phase may not be too long compared to an actual fall, so as to distinguish from ongoing activities such as exercise. In fact, actual fall events usually encompass a specific time frame, such as between about 0.25 seconds and about 15 seconds, or between about 0.5 seconds and about 5 seconds. In some implementations, if the duration of time of the during-fall phase is not within the minimum threshold value and the maximum threshold value, then the potential fall event can be rejected.

At block 120 of the process 100, a determination is made whether a potential fall event is a fall event based at least in part on the one or more extracted statistical features. If the extracted statistical features are indicative of a fall event, then the potential fall event is a fall event. Otherwise, the potential fall event can be an activity of daily life. In some implementations, determining whether a potential fall event is a fall event is based on the one or more extracted statistical features and a classifier trained using a machine-learning algorithm. A machine-learning algorithm can be used to train a classifier to classify events as actual falls or activities of daily living (i.e., non-falls). In some implementations, determining whether a potential fall event is a fall event is described further in a process 300 in FIG. 3.

Figure 3:
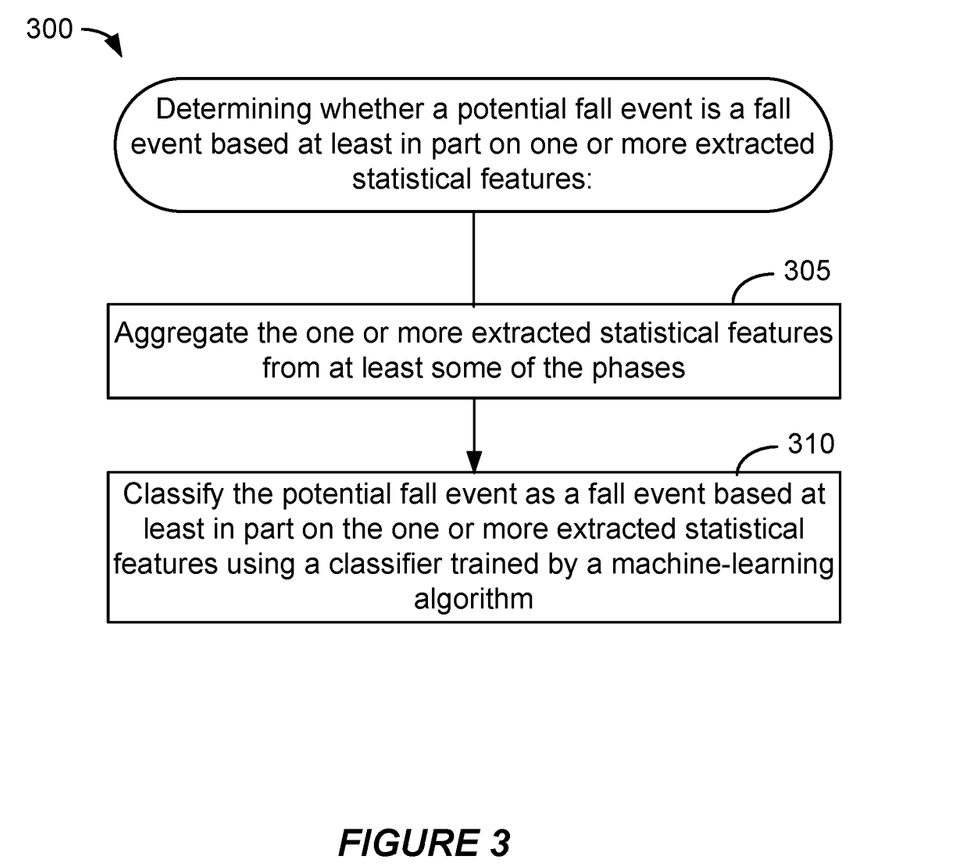
FIG. 3 shows a flow diagram illustrating an example process for determining whether a potential fall event is a fall event based at least in part on one or more extracted statistical features according to some implementations.

FIG. 3 shows a flow chart illustrating an example process for determining whether a potential fall event is a fall event based at least in part on one or more extracted statistical features according to some implementations. The process 300 may be performed in a different order or with different, fewer, or additional operations. In some implementations, the blocks of the process 300 may be performed by a device shown in FIG. 5, or by a device shown in FIG. 6, as described below. In some implementations, the blocks of the process 300 may be implemented, at least in part, according to software stored on one or more non-transitory computer readable media.

An example classifier of the process 300 predicts whether a potential fall event is a fall event based at least in part on the one or more extracted statistical features. At block 305 of the process 300, the one or more extracted statistical features from at least some of the phases are aggregated. Each of the extracted statistical features contributes to jointly determine whether a potential fall event is a fall event.

In some implementations, aggregation of the one or more extracted statistical features can include calculating a metric based on the one or more extracted statistical features. In some implementations, calculating the metric comprises a linear combination of the extracted statistical features. In some implementations, calculating the metric comprises a non-linear combination of the extracted statistical features. In some implementations, coefficients can be assigned to each of the extracted statistical features in the metric so that certain statistical features are more weighted than others. A classifier can be trained to classify whether a fall event has occurred from data (e.g., acceleration data, angular velocity data, or orientation data) of a plurality of different fall events and/or a plurality of different non-fall events. In other words, previous fall events and non-fall events can be used to train the classifier. The classifier can be trained to classify fall events using a suitable algorithm from among decision trees, random forest, boosting, support vector machines, neural networks, logistic regression, etc. In some implementations, the classifier can be trained to classify fall events using logistic regression. Coefficients to statistical features can be assigned based on the sensitivity of statistical features, where some statistical features may be more sensitive to detecting falls than others based on the different fall events and non-fall events. The metric can be calculated as a linear or non-linear combination of the extracted statistical features weighted by the assigned coefficients. The calculated metric can serve as an input for the classifier. The classifier can use a suitable algorithm such as logistic regression to classify whether the potential fall event is a fall event.

At block 310 of the process 300, the potential fall event is classified as a fall event based at least in part on the one or more extracted statistical features using a classifier trained by a machine-learning algorithm. The process 300 at block 310 uses the classifier to classify a potential fall event as either an actual fall event or an activity of daily living. In some implementations, the classifier uses logistic regression to predict whether the one or more extracted statistical features of the potential fall event sufficiently show that a fall event has occurred or not. In some implementations, the one or more extracted statistical features of the potential fall event can be indicative of the severity of the fall. In some implementations, if the classifier classifies the potential fall event as a fall event, an alarm signal can be generated.

Figure 5:
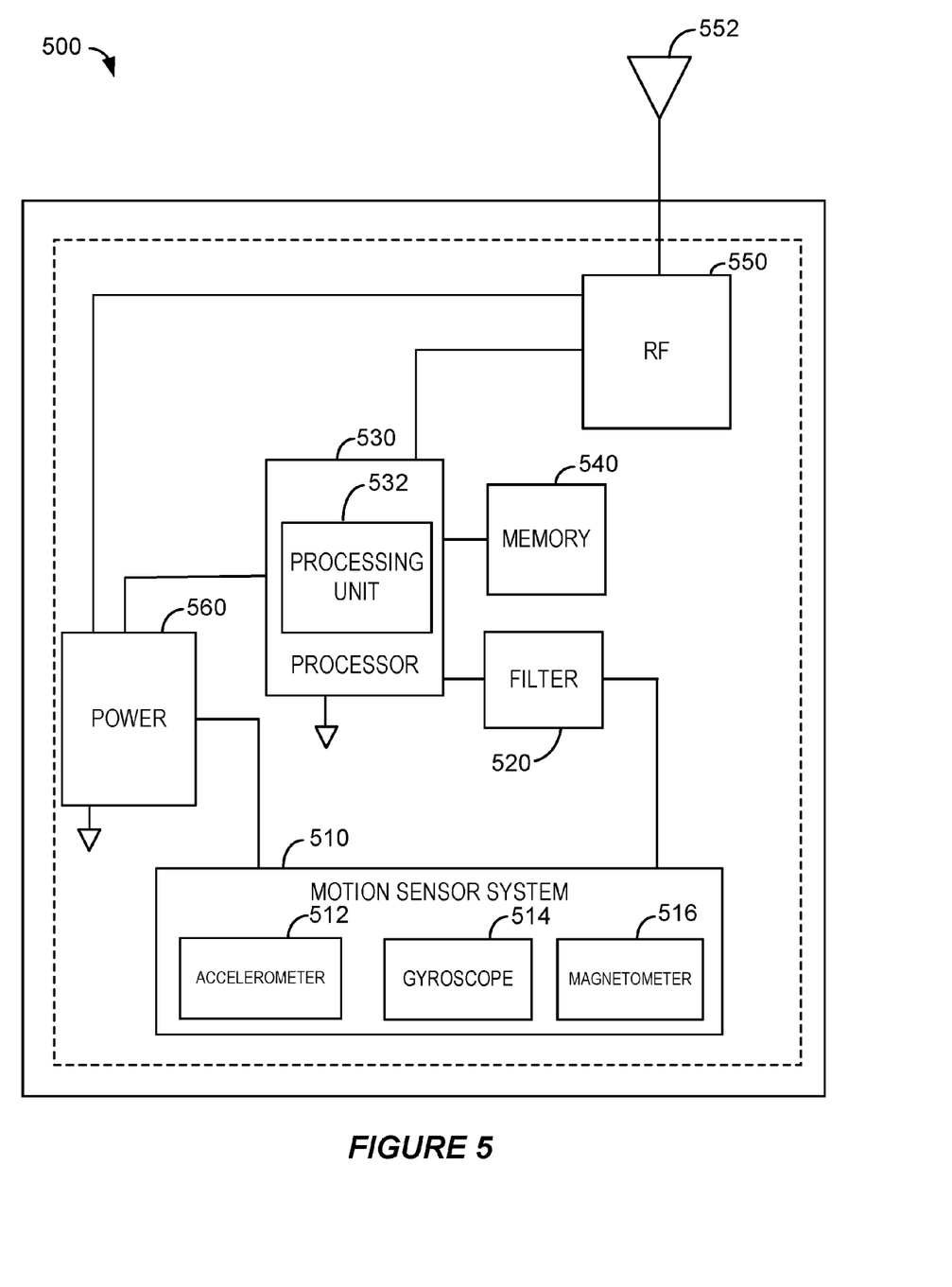
FIG. 5 shows a block diagram representation of components of an example fall detection device according to some implementations.

FIG. 5 shows a block diagram representation of components of an example fall detection device according to some implementations. As with other implementations disclosed herein, the number of elements and types of elements shown in FIG. 5 are merely by way of example. Other implementations may have more, fewer, or different elements. In the implementation in FIG. 5, the fall detection device 500 includes a motion sensor system 510, filter 520, a processor 530, a memory 540, a radio-frequency (RF) unit 550 coupled to an antenna 552, and a power supply 560.

In some implementations, the motion sensor system 510 includes one or more motion sensors 512, 514, and 516. The one or more motion sensors can include one or more accelerometers 512 that may be used to obtain acceleration data of a user. Optionally, the motion sensor system 510 can include one or more gyroscopes 514 and one or more magnetometers 516. The one or more gyroscopes 514 can provide measurements of angular acceleration, angular velocity, or rotation. The one or more magnetometers 516 can provide measurements of magnetic field or force. One or both of the gyroscopes 514 and the magnetometers 516 can provide the orientation of the user. Additionally, the one or more of the sensors 512, 514, and 516 can provide other motion-related information of the user, such as the type of motion of the user, the direction of motion of the user, the position of the fall detection device 500, instantaneous and average velocities and accelerations of the user, etc. In some implementations, the motion sensor system 510 includes all of the motion sensors 512, 514, and 516 described above. In some other implementations, the motion sensor system 510 includes a subset of the motion sensors 512, 514, and 516 described above. For example, the motion sensor system 510 may include only the one or more accelerometers 512 to reduce power consumption in the fall detection device 500.

The motion sensor system 510 may access acceleration data of the user and pass the acceleration data through a filter 520. The filter 520 can remove certain frequencies that fall outside a desired frequency range so that the acceleration data includes acceleration data encompassing normal activities and falls. In some implementations, the filter 520 can be a low-pass filter to remove high-frequency signals and smooth out the acceleration data. In addition, the filter 520 can serve to remove gravity and noise.

The motion sensor system 510 and the filter 520 may be coupled to the processor 530 so that the processor 530 may control or receive acceleration data. In some implementations, the processor 530 may control or receive additional data from the motion sensor system 510, such as angular velocity data and orientation data. The processor 530 may be dedicated hardware specifically adapted to perform a variety of functions for the fall detection device 500. In some implementations, the processor 530 may be or include a programmable processing unit 532 that may be programmed with processor-executable instructions. In some implementations, the processor 530 may be a programmable microprocessor, microcomputer, or multiple processor chip or chips that can be configured by software instructions to perform a variety of functions for the fall detection device 500. In some implementations, the processor 530 may be a combination of dedicated hardware and a programmable processing unit 532.

The processor 530 may be configured to access and process output signals from the motion sensor system 510 and the filter 520, such as acceleration data of the user. Using the acceleration data, the processor 530 may be configured to determine if a fall event has occurred. The processor 530 may perform calculations to segment the acceleration data using a segmentation algorithm. The processor 530 may further perform calculations using a CUSUM algorithm to segment the acceleration data and identify a potential fall event. The processor 530 may also extract and aggregate statistical features from the segmented acceleration data, and apply a classifier to determine if an actual fall event has occurred based on the extracted statistical features. The classifier may be trained using a machine-learning algorithm.

Various operations of the processes 100, 200, and 300 may be performed by the fall detection device 500. In some examples, one or more of the processes 100, 200, and 300 may be performed by the fall detection device 500 that includes the processor 530. In some implementations, the processor 530 can be coupled to the one or more motion sensors 512, 514, and 516 and can analyze the acceleration data. The processor 530 can be configured to: segment the acceleration data to identify a potential fall event, extract one or more statistical features from the segmented acceleration data, and determine whether a potential fall event is a fall event based at least in part on the one or more statistical features. In segmenting the acceleration data, the processor 530 can be configured to determine a cumulative sum for the acceleration data, where the cumulative sum is based on acceleration value being greater than or less than a first acceleration threshold value, and identify a potential fall event if the cumulative sum is greater than the cumulative sum threshold value. By way of example, the cumulative sum can be calculated using a CUSUM algorithm: CUSUM[i]=max(0, acceleration[i]+CUSUM[i−1]−$A_{th1}$), where CUSUM[0]=0, and where $A_{th1}$ is the first acceleration threshold value and acceleration[i] is the acceleration value at time [i], and where i>0. In some implementations, after the cumulative sum reaches a cumulative sum threshold value at $C_{th}$, $A_{th1}$ can be replaced by a second acceleration threshold value ($A_{th2}$).

In implementations for determining whether a potential fall event is a fall event based on the one or more statistical features, the processor 530 for analyzing the acceleration data can be configured to aggregate the one or more extracted statistical features from at least some of the phases, and classify the potential fall event as a fall event based at least in part on the one or more extracted statistical features using a classifier trained by a machine-learning algorithm. In some implementations, the processor 530 can be configured to classify the potential fall event as a fall event using a classifier trained using logistic regression. In some implementations, the processor 530 can be configured to calculate a metric using a linear or non-linear combination of the extracted statistical features weighted by assigned coefficients. The calculated metric can serve as an input for the classifier.

In some implementations, a memory 540 may store processor-executable instructions and/or outputs from the motion sensor system 510. In some implementations, the memory 540 may be a volatile memory, non-volatile memory (e.g., flash memory), or a combination thereof. In some implementations, the memory 540 may include internal memory included in the processor 530, memory external to the processor 530, or a combination thereof. The memory 540 may be coupled to the processor 530. In some implementations, the memory 540 may store data related to the segmentation algorithm and the machine-learning algorithm. For example, the processor 530 may access data regarding the first acceleration threshold value, the second acceleration threshold value, and the cumulative sum threshold value stored in the memory 540. The processor 530 may also store data in the memory 540 regarding the acceleration data and the extracted statistical features of the user for training the classifier using a machine-learning algorithm.

In some implementations, the processor 530 may be coupled to an RF unit 550 in order to communicate an alarm signal if a fall event has been determined. Upon determining that a potential fall event is a fall event, an alarm signal can be generated in the processor 530 and sent to the RF unit 550. In some implementations, the alarm signal can be communicated to a remote device for alerting a call center or caregiver. In some implementations, the RF unit 550 may be a transmitter-only or a two-way transceiver. The RF unit 550 may operate in one or more frequency bands depending on the supported type of communications.

In some implementations, one or more of the motion sensor system 510, the filter 520, the processor 530, the memory 540, the RF unit 550, and any other electronic components of the fall detection device 500 may be powered by the power supply 560. The power supply 560 may be a battery, a solar cell, and other suitable power sources for harvesting power.

Figure 6:
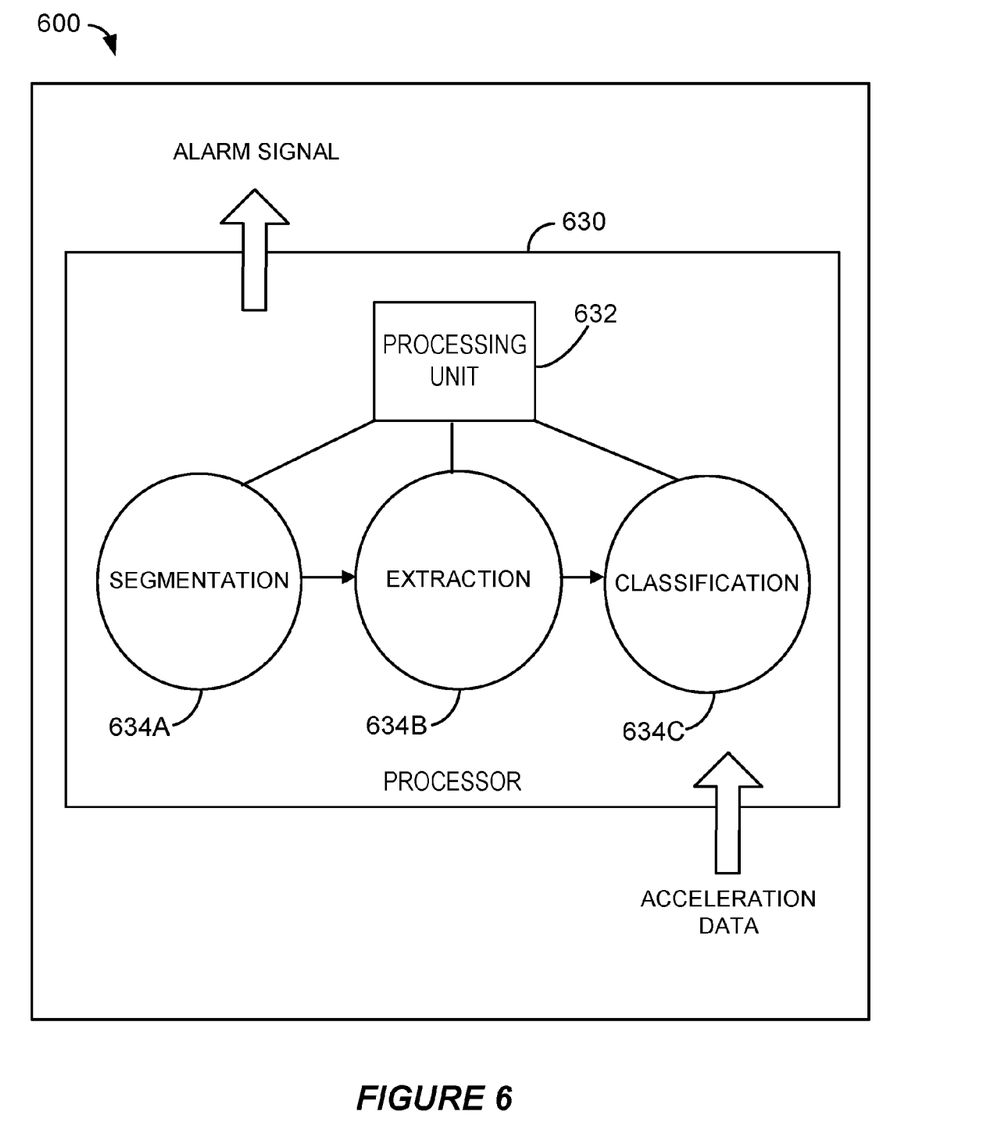
FIG. 6 shows a block diagram representation of a processor in a fall detection device and associated steps performed by the processor according to some implementations.

FIG. 6 shows a block diagram representation of a processor in a fall detection device and associated steps performed by the processor according to some implementations. The fall detection device 600 can include at least a processor 630, where the processor 630 can control several of the operations of the fall detection device 600. The fall detection device 600 can include one or more additional components as described in the fall detection device 500 of FIG. 5, such as one or more motion sensors 512, 514, and 516, filter 520, memory 540, RF unit 550 coupled to antenna 552, and power supply 560.

The processor 630 may be a combination of dedicated hardware, such as filters, gates, analog-to-digital conversion, etc., and a processing unit 632 configured to perform various operations. The processing unit 632 may be programmed with processor-executable instructions. In some implementations, the processing unit 632 can be configured by software instructions to perform a variety of functions for the fall detection device 600.

Various illustrative logics, logical blocks, modules, circuits, and algorithm steps described in connection with the implementations disclosed herein may be implemented as electronic hardware, computer software, or combinations of both. The interchangeability of hardware and software has been described generally, in terms of functionality, and illustrated in the various illustrative components, blocks, modules, circuits, and steps described above. The interchangeability of hardware and software can also be described, in terms of functionality, and illustrated in the various illustrative components, blocks, modules, circuits, and steps 634a, 634b, and 634c. Whether such functionality is implemented in hardware or software depends on the particular application and design constraints imposed on the system or device.

As shown in FIG. 6, acceleration data is received by the processor 630. In some implementations, the acceleration data can be filtered and normalized. The acceleration data can be received from one or more motion sensors, including but not limited to one or more accelerometers. The processing unit 632 processes the acceleration data through a series of logics, logical blocks, modules, circuits, and/or algorithm steps shown in blocks 634a, 634b, and 634c. At segmentation block 634a, the processing unit 632 segments the acceleration data into at least three phases to identify a potential fall event, where the at least three phases include but are not limited to (1) a before-fall phase, (2) a during-fall phase, and (3) an after-fall phase, where the during-fall phase includes the potential fall event. In some implementations, the segmentation block 634a applies a segmentation algorithm to segment the acceleration data. The segmentation algorithm can include a CUSUM algorithm, where the CUSUM algorithm can be used to identify the potential fall event and segment the acceleration data. At extraction block 634b, the processing unit 632 extracts one or more statistical features from at least some of the phases or each of the phases. Examples of statistical features include: variance, maximum, minimum, $75^{th}$ percentile, $25^{th}$ percentile, mean, median, mean crossing rate, absolute area, or any combination thereof. In some implementations, the acceleration data in each of the phases can be analyzed to extract statistical features from each of the phases. At classification block 634c, the processing unit 632 classifies the potential fall event as a fall event based on an aggregation of the extracted statistical features and a classifier. A machine-learning algorithm can train the classifier by applying a suitable algorithm such as logistic regression, where the classifier can determine whether the candidate fall event is an actual fall event. In some implementations, a metric can be calculated based on the extracted statistical features, where the calculated metric includes a linear or non-linear combination of the extracted statistical features weighted by assigned coefficients. After the classification determines that a fall event has occurred, an alarm signal may be generated. In some implementations, the alarm signal may be sent to an RF unit for communicating to an external device.

The hardware and data processing apparatus used to implement the various illustrative logics, logical blocks, modules, and circuits described in connection with the aspects disclosed above and disclosed in blocks 634a, 634b, and 634c may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the function described herein. The processing unit 632 may be a microprocessor, or, any conventional processor, controller, microcontroller, or state machine. The processing unit 632 also may be implemented as a combination of computing devices, such as a combination of a DSP and a microprocessor, a plurality of microprocessors, one or more microprocessors with a DSP core, or any other such configuration. In some implementations, particular steps and methods may be performed by circuitry that is specific to a given function.

In one or more aspects, the functions described may be implemented in hardware, digital electronic circuitry, computer software, firmware, including the structures disclosed in this specification and their structural equivalents, or in any combination thereof. Implementations of the subject matter described in this specification also can be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium. The steps of a method or algorithm disclosed herein may be implemented in a processor-executable software module which may reside on a computer-readable medium. Computer-readable media includes both computer storage media and communication media including any medium that can be enabled to transfer a computer program from one place to another. A storage media may be any available media that may be accessed by a computer. By way of example, and not limitation, such computer-readable media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above also may be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Additionally, certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. Moreover, various ones of the described and illustrated operations can itself include and collectively refer to a number of sub-operations. For example, each of the operations described above can itself involve the execution of a process or algorithm. Furthermore, various ones of the described and illustrated operations can be combined or performed in parallel in some implementations. Similarly, the separation of various system components in the implementations described above should not be understood as requiring such separation in all implementations. As such, other implementations are within the scope of the following claims. In some cases, the actions recited in the claims can be performed in a different order and still achieve desirable results.

What is claimed is:

1. A method of identifying a fall event using a wearable electronic monitoring device, wherein the wearable electronic monitoring device includes one or more processors and one or more motion sensors coupled to the one or more processors, the method comprising:
  accessing, from the one or more motion sensors of the wearable electronic monitoring device, acceleration data indicative of motion of a user of the wearable electronic monitoring device;
  segmenting, by the one or more processors, the acceleration data into at least three phases using a segmentation algorithm to identify a potential fall event, comprising:
    determining a cumulative sum for the acceleration data; and
    identifying the potential fall event in the acceleration data where the cumulative sum is greater than a cumulative sum threshold value, wherein the acceleration data is segmented into the at least three phases using the cumulative sum for the acceleration data;
  extracting, by the one or more processors, one or more statistical features from the segmented acceleration data;
  determining, by the one or more processors, whether the potential fall event is a fall event based at least in part on the one or more extracted statistical features,
  generating an alarm signal from the wearable electronic device based on the one or more processors determining the potential event to be a fall event.

2. The method of claim 1, wherein the at least three phases include (i) a before-fall phase, (ii) a during-fall phase, and (iii) an after-fall phase, and wherein the during-fall phase includes the potential fall event.

3. The method of claim 2, further comprising:
  analyzing the duration of time of the during-fall phase, wherein determining whether the potential fall event is a fall event is based at least in part on the duration of time of the during-fall phase.

4. The method of claim 2, wherein the one or more statistical features include one or more of the following: variance, maximum, minimum, $75^{th}$ percentile, $25^{th}$ percentile, mean, median, mean crossing rate, absolute area, or any combination thereof.

5. The method of claim 4, wherein the one or more statistical features include: a mean crossing rate of acceleration extracted from the during-fall phase and variance of acceleration extracted from the after-fall phase.

6. The method of claim 4, further comprising:
  accessing angular velocity data and orientation data from the one or more motion sensors; and
  segmenting the angular velocity data and the orientation data into the at least three phases, wherein the one or more statistical features include: a mean crossing rate of acceleration extracted from the during-fall phase, a maximum acceleration extracted from the during-fall phase, an absolute area of acceleration extracted from the after-fall phase, a variance of angular velocity extracted from the during-fall phase, a maximum of angular velocity extracted from the during-fall phase, a minimum of angular velocity extracted from the after-fall phase, a median of orientation extracted from the after-fall phase, or any combination thereof.

7. The method of claim 1, wherein the acceleration data is segmented where the cumulative sum is zero before increasing in value and where the cumulative sum is zero after decreasing in value.

8. The method of claim 1, further comprising:
  processing, by a low-pass filter in the wearable electronic monitoring device, the acceleration data prior to segmenting the acceleration data.

9. The method of claim 1, wherein the cumulative sum is calculated using acceleration values greater than or less than a first acceleration threshold value.

10. The method of claim 9, wherein the first acceleration threshold value and the cumulative sum threshold value are identified by a machine-learning algorithm.

11. The method of claim 1, wherein the cumulative sum has the formula:

$$\text{CUSUM}[i]=\max(0,\text{CUSUM}[i-1]+\text{acceleration}[i]-A_{th1}),$$

wherein CUSUM[0]=0, and wherein $A_{th1}$ is the first acceleration threshold value and acceleration[i] is an acceleration value at time [i], and wherein i>0.

12. The method of claim 1, wherein determining whether a potential fall event is a fall event comprises:

aggregating the one or more statistical features from the segmented acceleration data;

calculating a metric based on the one or more statistical features; and classifying the potential fall event as a fall event based at least in part on the calculated metric.

13. The method of claim 12, wherein the metric is calculated as a linear or non-linear combination of the extracted statistical features weighted by coefficients.

14. The method of claim 12, wherein the potential fall event is classified using a classifier trained by a machine-learning algorithm.

* * * * *